US009295775B2

(12) United States Patent
Duffour et al.

(10) Patent No.: US 9,295,775 B2
(45) Date of Patent: Mar. 29, 2016

(54) DEVICE FOR INJECTING CONTRAST MEDIA

(75) Inventors: Hervé Duffour, Lausanne (CH); Frédéric Neftel, Lausanne (CH)

(73) Assignee: BRACCO INJENEERING S.A., Lausanne (CH)

( * ) Notice: Subject to any disclaimer, the term of this patent is extended or adjusted under 35 U.S.C. 154(b) by 0 days.

(21) Appl. No.: 13/496,990

(22) PCT Filed: Sep. 13, 2010

(86) PCT No.: PCT/IB2010/054114
§ 371 (c)(1),
(2), (4) Date: Jun. 1, 2012

(87) PCT Pub. No.: WO2011/033440
PCT Pub. Date: Mar. 24, 2011

(65) Prior Publication Data
US 2012/0232383 A1    Sep. 13, 2012

(30) Foreign Application Priority Data

Sep. 18, 2009   (EP) .................................. 09170730

(51) Int. Cl.
  *A61B 6/00*   (2006.01)
  *A61M 5/00*   (2006.01)
  *A61M 5/14*   (2006.01)
  *A61M 5/142*  (2006.01)
(52) U.S. Cl.
  CPC ............. *A61M 5/007* (2013.01); *A61M 5/1408* (2013.01); *A61M 2005/14208* (2013.01)
(58) Field of Classification Search
  USPC .................. 600/431, 407; 604/30, 97, 99
  See application file for complete search history.

(56) References Cited

U.S. PATENT DOCUMENTS

| 5,590,654 | A  * | 1/1997  | Prince ............................ 600/420 |
| 2002/0183616 | A1 * | 12/2002 | Toews et al. ................... 600/432 |
| 2003/0078492 | A1 * | 4/2003  | Talpade ......................... 600/420 |
| 2004/0115731 | A1 * | 6/2004  | Hansen et al. .................. 435/7.1 |
| 2005/0085769 | A1 * | 4/2005  | MacMahon et al. ....... 604/96.01 |
| 2007/0213848 | A1   | 9/2007  | DeKemp et al. |
| 2007/0225813 | A1 * | 9/2007  | Haines ........................ 623/17.16 |

FOREIGN PATENT DOCUMENTS

| EP | 1867356       | 12/2007 |
| JP | 2009-529682   | 8/2009  |
| WO | WO2004006994  | 1/2004  |
| WO | 2007/104133   | 9/2007  |
| WO | 2008/085421   | 7/2008  |

OTHER PUBLICATIONS

English Translation of International Preliminary Report on Patentability (IPRP) for PCT/IB2010/054114, dated Apr. 11, 2012.
International Search Report for PCT/IB2010/054114 mailed Feb. 28, 2011.
Written Opinion of the International Searching Authority mailed Feb. 28, 2011.
Japanese Official Action with English-language Translation dated Jun. 24, 2014.
Russian Official Action with English-language Translation dated Nov. 11, 2014.

* cited by examiner

*Primary Examiner* — Joel F Brutus
(74) *Attorney, Agent, or Firm* — Nixon & Vanderhye P.C.

(57) ABSTRACT

The invention relates to a medical device for injecting contrast media including at least two separate vessels and immiscible contents inside one and/or both of the vessels, an injector and a distributor arranged such as to establish alternating communication between said vessels and said injector, said medical device being characterised in that it includes a means for providing said alternating communication at a frequency of 0.2 to 5 Hz.

9 Claims, 7 Drawing Sheets

DEVICE FOR INJECTING CONTRAST MEDIA

This application is the U.S. national phase of International Application No. PCT/IB2010/054114 filed 13 Sep. 2010 which designated the U.S. and claims priority to EP 09170730.7 filed 18Sep. 2009, the entire contents of each of which are hereby incorporated by reference.

FIELD OF THE INVENTION

The field of the invention is that of medical imaging, obtained by injecting contrast media and, more specifically, that of the injection of more or less dilute contrast media such as for X-ray imaging, CT scanners or MRI imaging.

PRIOR ART

The use of syringe driving injectors capable, from two syringes in parallel, of injecting a contrast medium at the same time as a saline solution, the purpose of this being to dilute the contrast medium, are already known at the present time.

U.S. Pat. Nos. 7,267,667 and 5,911,252 describe such devices. US 2007/213848 describes a mechanism (on/off valve) for the alternating injection of a radioactive compound into a saline solution. This mechanism therefore covers a method of eluting (rather than of diluting) the radioactive compound in a saline solution. This elution method—more specifically elution control method—provides control over the activity of the radioactive compound. If this activity is too weak at the detector, the saline solution enters the reservoir containing the radioactive compound and takes up a certain quantity thereof by elution. As soon as the activity measured by the detector returns to the desired value, the valve closes and the saline solution passes only through the "bypass" line.

GENERAL OVERVIEW OF THE INVENTION

In the invention, the solution to the aforementioned problem is to inject contrast medium into an organ that is to be analyzed in such a way that the concentrations of such contrast medium vary over the course of time and/or with the region of the organ being analyzed at the moment of image acquisition.

The present invention offers several advantages, particularly the ability to make such concentration modifications inside the organ at a precise moment corresponding to image acquisition, without having to resort to two injectors used in parallel, at lower cost and with a lower risk (notably of error and/or of contamination) to the patient.

It should be noted that the present invention differs from the teaching of US 2007/213848 in that the concentration of the contrast medium is varied by alternating the injections of "saline solution/contrast medium" in such a way that the mixing—and therefore the desired concentration—is obtained before it reaches the heart.

The invention can also be applied to the amplification of an extravasation detection signal, for example using ultrasound, situated downstream of the point of injection into the patient as a result of the change in the nature or concentration of the injected liquid. Thus it is possible to make sure that the liquid has indeed been injected into the vessels concerned thereby excluding any potential extravasion if the injection needle is withdrawn from the patient's vein during said injection. If use is being made of an extravasion detector, because the signal is more or less constant, it is sometimes no longer possible to ensure that the signal is measuring correctly (false positive, or even false negative). By modifying the nature of the liquid during the course of injection (which corresponds to a change in the measured signal), and using any correspondence there might be between this measured change and the injection sequence, it is possible to ensure that the extravasation detector is operating correctly and from this deduce that the injection flow is normal, excluding any extravasion. In the event of failure to measure this signal which is variable as a function of the frequency of injection of the two alternating liquids, it is possible from this to deduce either that the measurement probe is incorrectly positioned or that extravasion is taking place and, in both instances, to interrupt injection.

DETAILED DESCRIPTION OF THE INVENTION

The invention is described in greater detail below through examples illustrated by the following figures:

FIGS. 1A, 1B and 1C give an example of an injector programming interface, featuring the various possible combinations with, in FIG. 1A, the option to choose between the injection of contrast, saline or dilution "diluject"; in FIG. 1B the dilution options (15%, 20%, 25% or 30%); and in FIG. 1C, the dilution phase in a diagram.

Figure 1A:
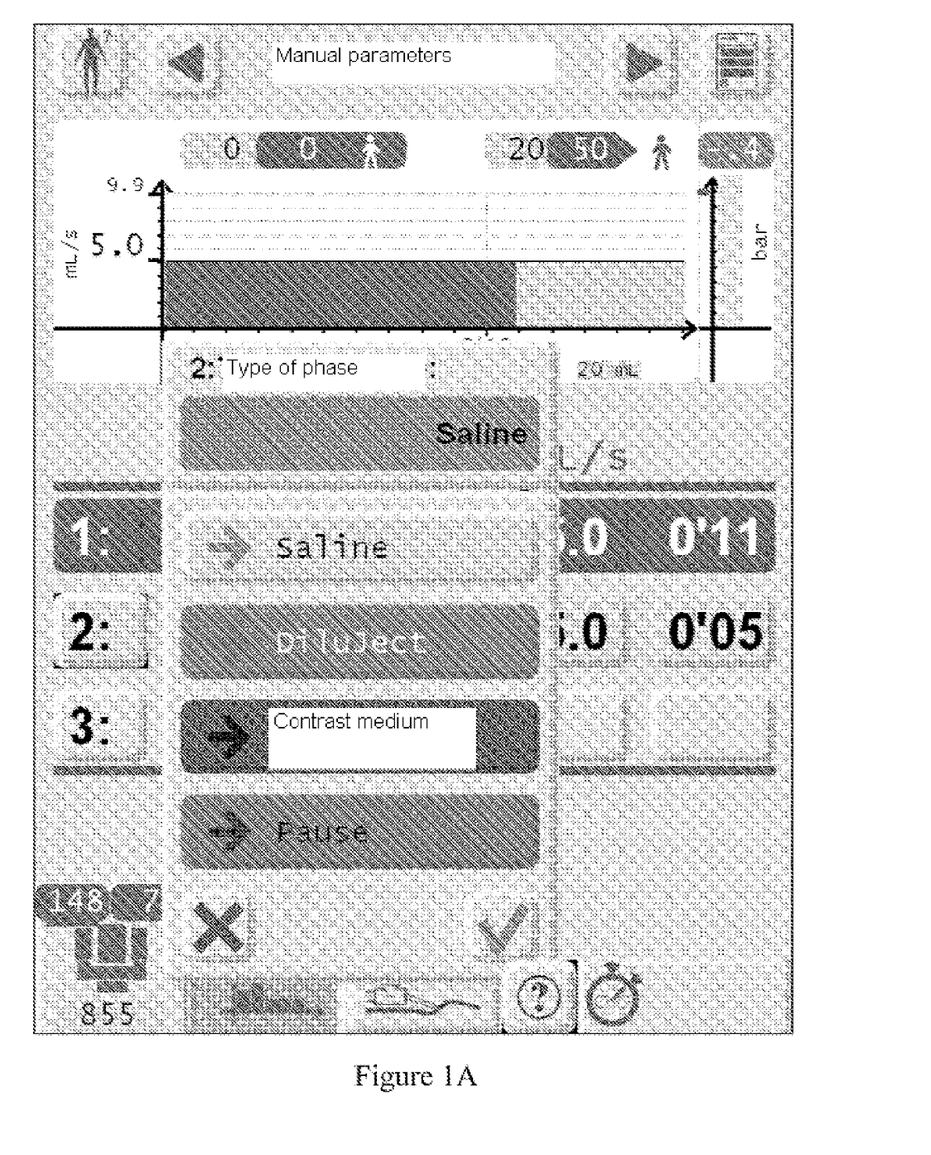
Figure 1B:
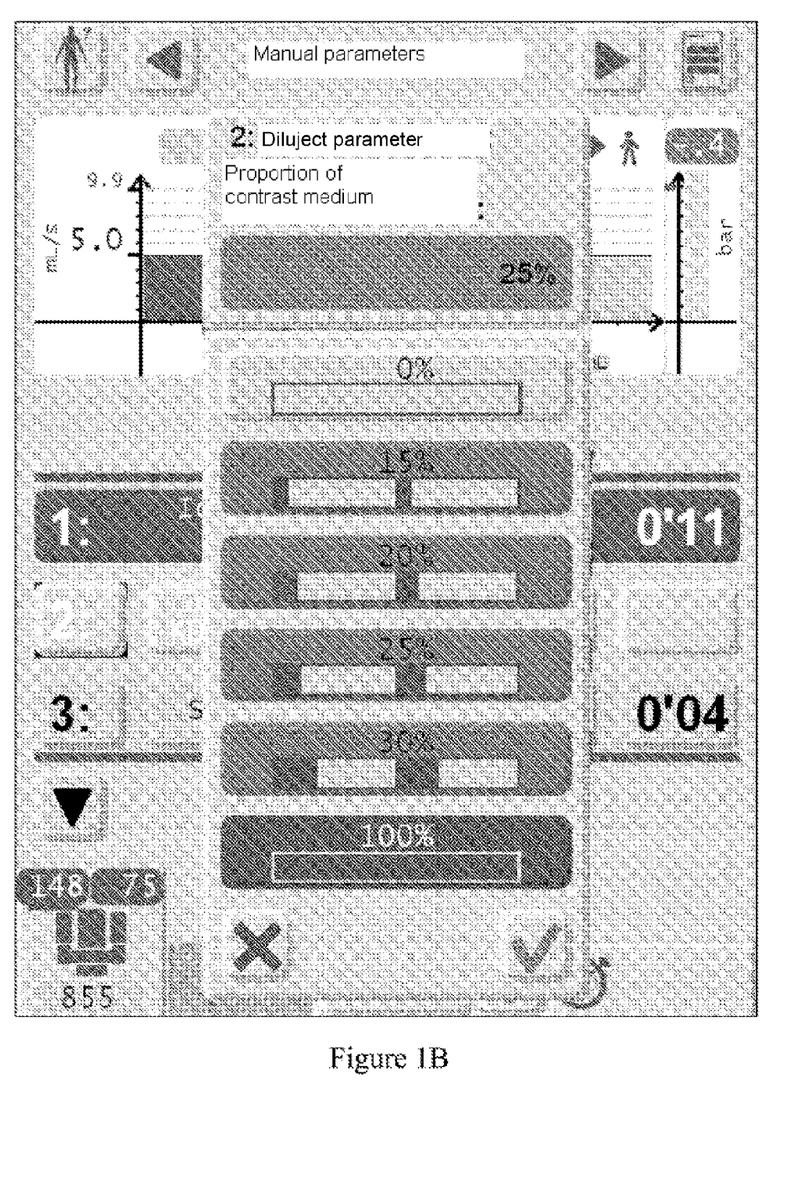
Figure 1C:
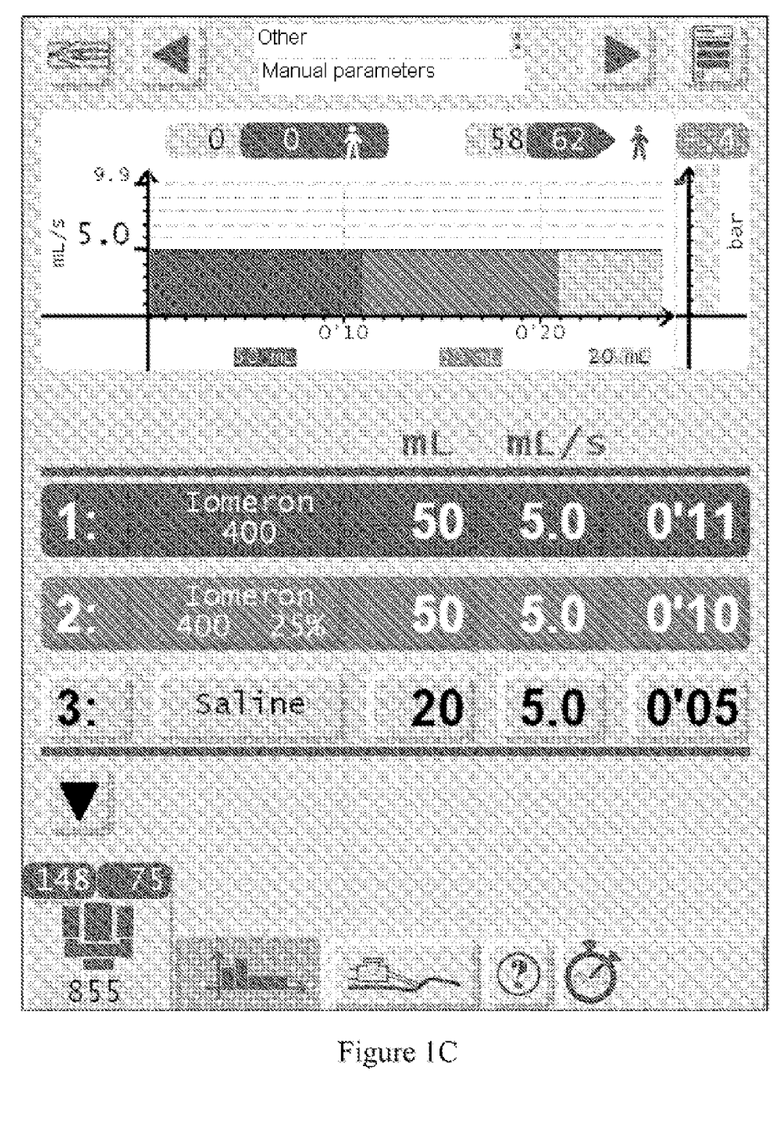
Figure 2A:
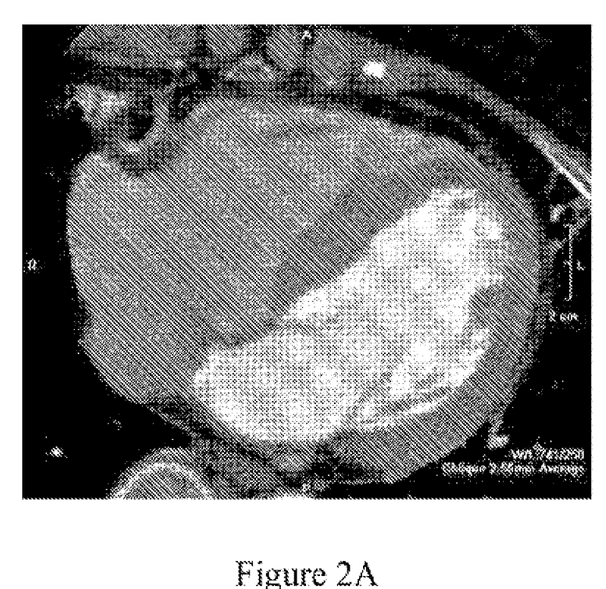
FIGS. 2A and 2B depict images obtained with a dilution of 15% and a flow rate of 4 ml/s (2A and 2B) and show an optimum dilution in the heart with a difference, in this example, between the concentration in the right side of the heart and the left side of the heart.
Figure 2B:
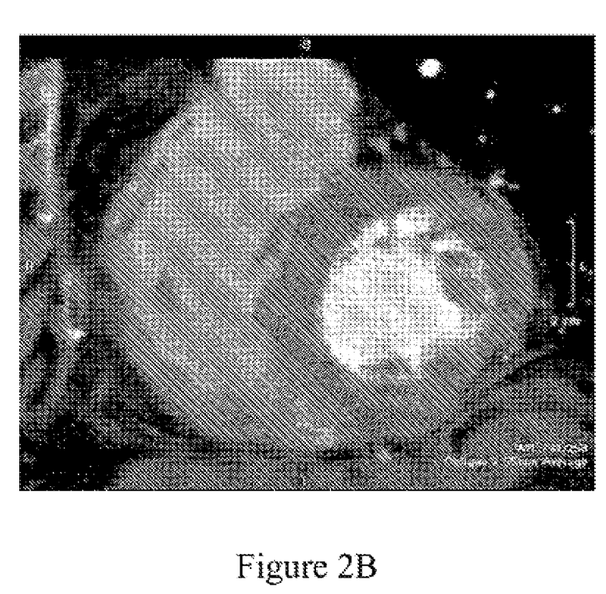
Figure 3A:
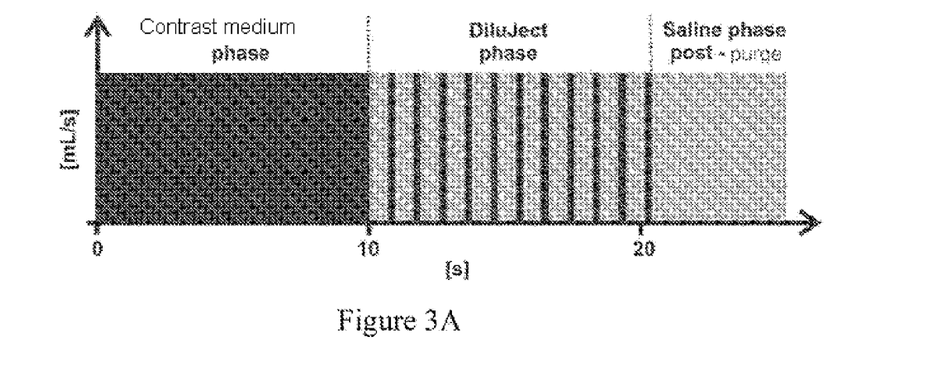
FIGS. 3A-3C (3A fixed dilution, 3B dilution at variable flow rate and frequency, 3C two examples of dilutions at different flow rates) depict examples of injection cycles with different dilution modes.
Figure 3B:
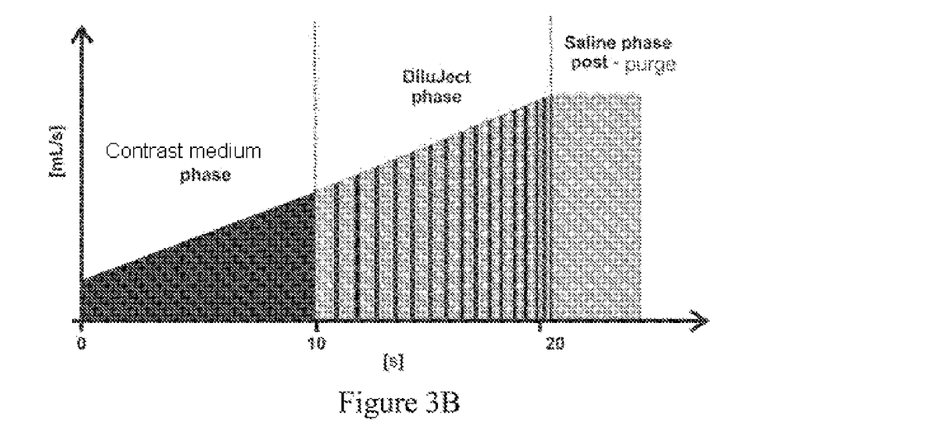
Figure 3C:
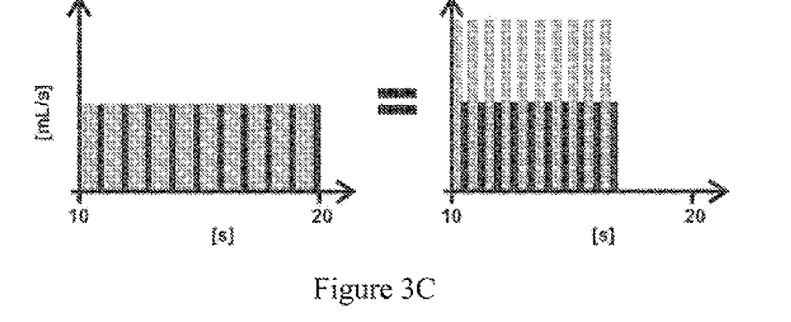
Figure 4A:
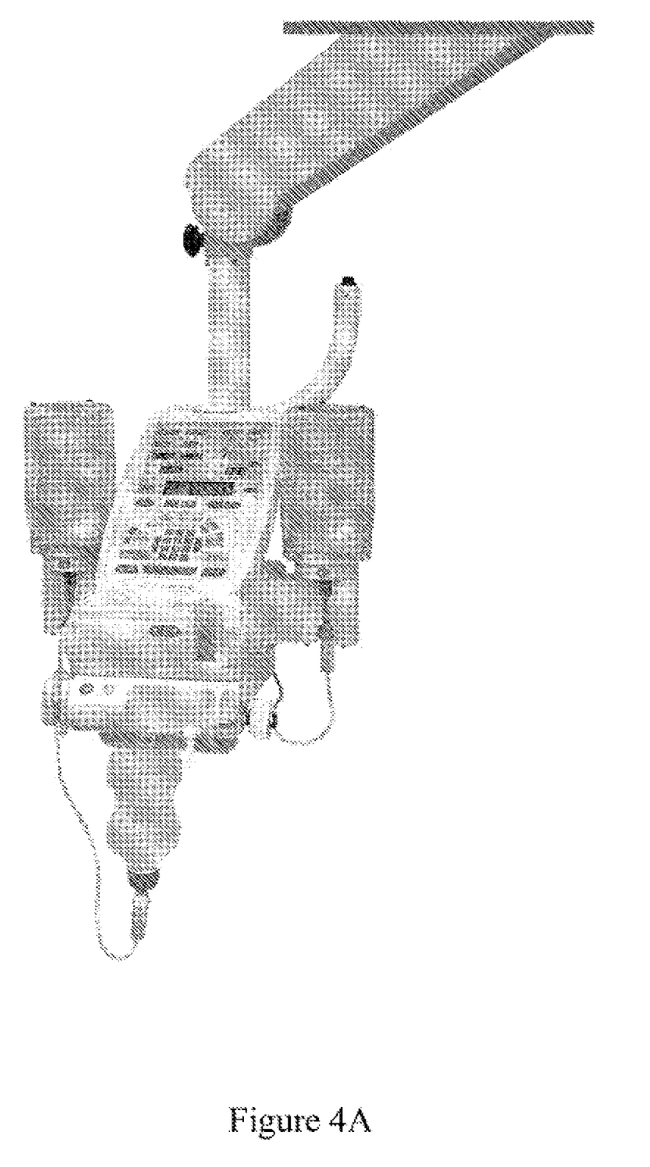
FIGS. 4A and 4B depict an injector that can be used to carry out the invention.
Figure 4B:
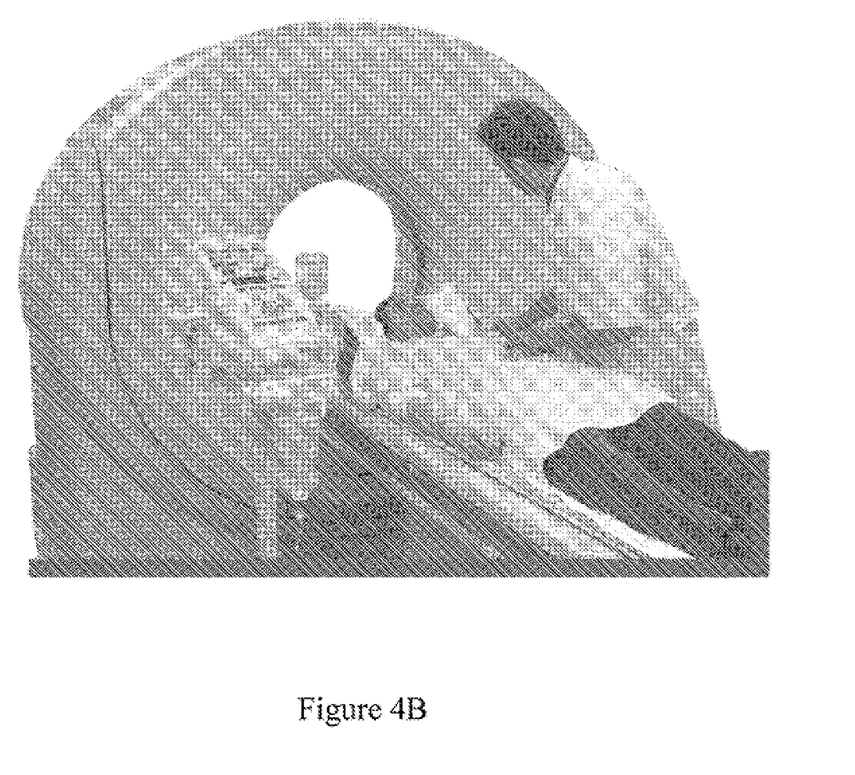

One of the objectives of the present invention is to obtain a contrast medium dilution (either by using two different contrast media or by using one contrast medium and a saline solution or any other solution that has no effect on the contrast during the examination, such as a non-iodized pharmaceutical solution) before it reaches the target organ (for example, the right side of the patient's heart), in order to be able to improve the acquisition of data relating to the anatomy and operation of the organ being analyzed (in the case of the heart: to view the septum, the coronary blood vessels, better calculate the ejection fraction of the heart; knowing that in order to do this the left-hand side of the heart is preferably filled with contrast while the right-hand side of the heart is filled with a dilute contrast solution) either at the same time or at the respective moment when images are acquired respectively in the organ concerned (first the left side of the heart then the right side).

To do this, the invention preferably involves successively injecting into the patient's vein phases of contrast medium alternating with phases of injection of saline solution or of a more weakly concentrated contrast medium, the purpose of this being to obtain a mixing of the various phases which can take place within the patient's cardiovascular system before it reaches the heart or the organ that is to be analyzed. The invention may advantageously be used in CT scanning or in MRI. In order to obtain effective dilution it is necessary for the frequency to be high enough that mixing can take place in the patient's cardiovascular system before it reaches the target organ. In the case of the heart, it is desirable to have a frequency quite close to cardiac frequency, typically of the order of 1 Hz, but that can also be effective between 5 Hz and 0.2 Hz.

Thus it is possible to dispense with a double injector and perform the dilution directly inside the patient's body using one single injector connected to two types of solutions of different concentrations (or one contrast solution and one saline solution) at a lower cost and involving fewer connections and manipulations which always represent a risk in terms of asepsis and of errors.

Typically, the desired percentage dilution to be obtained in the heart can be chosen (e.g. 15%, 20%, 25% or 30% dilution, which means that for 25% there will be just 25% contrast medium and 75% saline solution). In the case of a 25% dilution, it is possible for example to choose a phase of 1 ml of contrast followed by a phase of 3 ml of saline, the two phases representing a cycle which is repeated according to the total volume that is to be injected (e.g. for 20 ml injected 5 successive cycles will be carried out in the example described). The flow rate in this case is the same for the saline solution and the contrast solution (e.g. 4 ml/s). Alternatively, it is also possible to vary the flow rate in order to obtain the same dilution effect but with a modified volume. Thus, in the example described above, the 3 ml of the saline solution phase can be replaced by a 1.5 ml phase with a flow rate reduced by half (in the example 2 ml/s instead of 4 ml/s). It is also possible to elect to vary the flow rate of the contrast solution and perform other combinations that have the effect of modifying the contrast ratios in the target organ. It is also possible to elect to vary the respective flow rates and/or volumes of saline and of contrast in each cycle, for example progressively, in order to obtain dynamic images with concentrations that vary during the examination and/or image acquisition period, using algorithms that can adopt any suitable mathematical form.

In order to produce such a device, use is preferably made of a processor capable of managing the alternation between the two reservoirs, for example by commanding the opening and closing of clamps situated between each of the reservoirs and the injection device (for example a peristaltic cassette).

The invention claimed is:

1. A medical device for separately injecting into a patient's cardiovascular system during an imaging procedure of a targeted internal part of a patient's body a first fluid as a contrast medium and a second fluid which changes concentration of the first fluid so as to achieve a mixing of the first fluid and second fluid inside the patient's cardiovascular system and thereby obtain a contrast medium of selected concentration at the targeted internal part of the patient's body when imaged, wherein the medical device comprises:

at least first and second separate reservoirs respectively containing fluids which cannot mix with one another in either one of the at least first and second separate reservoirs, wherein the first separate reservoir contains the first fluid as the contrast medium and the second separate reservoir contains the second fluid which changes concentration of the first fluid when mixed therewith, an injector adapted to bringing the at least first and second separate reservoirs and the first fluid and the second fluid contained therein into fluid communication with the patient's cardiovascular system, a directional control valve system operatively connected to each of the at least first and second separate reservoirs so as to place the at least first and second separate reservoirs and the first and second fluids respectively contained therein alternately in fluid communication with the injector to thereby cause separate alternating injections of the first fluid and the second fluid through the injector and into the patient's cardiovascular system, and a controller for controllably achieving a contrast medium of selected concentration in the targeted internal part of the patient's body being imaged by operating the directional control valve system to provide alternating communication between each of the at least first and second separate reservoirs and the injector for a minimum of two consecutive cycles to cause respective separate alternating injections of the first fluid and the second fluid through the injector and into the patient's cardiovascular system, the controller alternating communication between each of the at least first and second separate reservoirs at a sufficiently high frequency of 0.2 and 5 Hz in correlation with a cardiac frequency of the patient's cardiovascular system to cause separately injected first and second fluids to mix with one another in the patient's cardiovascular system in advance of the targeted internal part of the patient's body being imaged to thereby achieve a contrast medium of selected concentration at the targeted internal part when imaged.

2. The medical device as claimed in claim 1, wherein the controller establishes the alternating communication between the at least first and second reservoirs at a frequency of around 1 Hz.

3. The medical device as claimed in claim 1, wherein the controller varies the frequency over time.

4. The medical device as claimed in claim 1, wherein each of the at least first and second reservoirs is capable of providing a continuous flow of the first fluid and the second fluid, respectively, of between 0.1 and 5 ml.

5. The medical device as claimed in claim 1, wherein the first reservoir contains a contrast medium and the second reservoir contains a saline solution.

6. The medical device as claimed in claim 1, wherein each of the first reservoir contains a first contrast medium and the second reservoir contains a second fluid contrast medium at a different concentration as compared to the first contrast medium.

7. The medical device as claimed in claim 6, wherein the second reservoir contains a second contrast medium of a lesser concentration as compared to the first contrast medium.

8. A medical device for separately injecting into a patient's cardiovascular system during an imaging procedure of a targeted internal part of a patient's body a first fluid as a contrast medium and a second fluid which changes concentration of the first fluid so as to achieve a mixing of the first fluid and the second fluid inside the patient's cardiovascular system and thereby obtain a contrast medium of selected concentration at the targeted internal part of the patient's body when imaged, wherein the medical device comprises:

at least first and second separate reservoirs respectively containing fluids which cannot mix with one another in either one of the at least first and second separate reservoirs, wherein the first separate reservoir contains the first fluid as a contrast medium and the second separate reservoir contains the second fluid capable of mixing with the first fluid to provide the contrast medium of selected concentration when mixed therewith, an injector adapted to bringing the at least first and second separate reservoirs and the first and second fluids contained therewithin into fluid communication with the patient's cardiovascular system, a directional control valve system comprising first and second clamps operatively connected to the at least first and second separate reservoirs, respectively, so as to place the at least first and second separate reservoirs and the first fluid and the second fluid respectively contained therein alternately in fluid communication with the injector to thereby cause separate alternating injections of the first fluid and the second fluid through the injector and into the patient's cardiovascular system, and a controller for controllably achieving a contrast medium of selected concentration in the targeted internal part of the patient's body being imaged by alternately operating the first and second clamps of the directional control valve system to provide alternating communication between each of the at least first and second separate reservoirs and the injector to cause respective separate alternating injections of the first fluid and the second fluid through the injector and into the patient's cardiovascular system, wherein the controller alternates communication between each of the at least first and second separate reservoirs at a sufficiently high frequency of 0.2 and 5 Hz in correlation with a cardiac frequency of the patient's cardiovascular system to cause the separately injected first and second fluids to mix with one another in the patient's cardiovascular system in advance of the targeted internal part thereof to achieve a contrast medium of selected concentration at the targeted internal part of the patient's body when imaged, and wherein the controller varies the frequency of the alternating communication between the at least first and second separate reservoirs for at least two cycles so as to inject separate discrete phases of contrast medium having first and second concentrations at the targeted internal part of the patient's body when imaged.

9. An imaging method for non-invasively imaging a targeted internal part of a patient's body comprising:

(a) providing first and second fluid reservoirs respectively containing first and second fluids which cannot mix with one another in either one of the first and second fluid reservoirs, wherein the first fluid reservoir contains a first fluid as a contrast medium and the second fluid reservoir contains a second fluid which changes concentration of the first fluid when mixed therewith;

(b) providing an injector in fluid communication with a patient's cardiovascular system and a directional control valve system for establishing separately alternating fluid communication between the first and second fluid reservoirs and the first and second fluids contained therewithin, respectively, and the injector;

(c) separately and alternately injecting through the injector and into the patent's cardiovascular system during an imaging procedure of the targeted internal part of the patient's body the first fluid as a contrast medium contained in the first fluid reservoir and the second fluid contained in the second fluid reservoir;

(d) allowing separately and alternately injected first and second fluids to mix with one another and thereby achieve a contrast medium of selected concentration in advance of the targeted internal part of the patient's body being imaged; and (e) conducting imaging when the contrast medium of selected concentration is at the targeted internal part of the patient's body, wherein step (c) is practiced by controlling the directional control valve to provide alternating communication between each of the first and second reservoirs and the injector for a minimum of two consecutive cycles to cause respective separate alternating injections of the first fluid and the second fluid through the injector and into the patient's cardiovascular system at a sufficiently high frequency of 0.2 and 5 Hz in correlation with a cardiac frequency of the patient's cardiovascular system to cause the separately injected first and second fluids to mix with one another in the patient's cardiovascular system in advance of the targeted internal part of the patient's body being imaged to achieve the contrast medium of selected concentration at the targeted internal part of the patient's body when imaged.

* * * * *